(12) United States Patent
Sotiriou

(10) Patent No.: US 7,648,454 B2
(45) Date of Patent: Jan. 19, 2010

(54) MAGNETIC THERAPY DEVICE

(76) Inventor: George Sotiriou, Trident Building 42 Academy St., Patchogue, NY (US) 11772

( * ) Notice: Subject to any disclaimer, the term of this patent is extended or adjusted under 35 U.S.C. 154(b) by 454 days.

(21) Appl. No.: 11/247,365

(22) Filed: Oct. 11, 2005

(65) Prior Publication Data
US 2007/0083074 A1    Apr. 12, 2007

(51) Int. Cl.
    *A61N 1/00*      (2006.01)
(52) U.S. Cl. ........................................................ 600/15
(58) Field of Classification Search ............... 600/8–15; 455/573, 574; 310/156.38; 340/870.31, 340/870.32, 870.37; 428/800, 900; 128/898, 128/899
See application file for complete search history.

(56) References Cited

U.S. PATENT DOCUMENTS

| | | | | |
|---|---|---|---|---|
| 4,228,387 A * | 10/1980 | Brown | ......................... | 318/696 |
| 4,340,890 A * | 7/1982 | Fritze | ..................... | 340/870.32 |
| 4,350,937 A * | 9/1982 | Miyazaki et al. | ............ | 388/816 |
| 4,537,181 A | 8/1985 | Shalhoob | | |
| 4,727,857 A * | 3/1988 | Horl | .............................. | 600/15 |
| 5,632,720 A | 5/1997 | Kleitz | | |
| 5,667,469 A | 9/1997 | Zhang | | |
| 5,762,599 A * | 6/1998 | Sohn | ........................... | 600/30 |
| 6,001,055 A | 12/1999 | Souder | | |
| 6,065,210 A | 5/2000 | Bove | | |
| 6,123,657 A | 9/2000 | Ishikawa | | |
| 6,155,966 A * | 12/2000 | Parker | ......................... | 600/13 |
| 6,231,497 B1 | 5/2001 | Souder | | |
| 6,238,333 B1 * | 5/2001 | Loos | .............................. | 600/9 |
| 6,245,006 B1 * | 6/2001 | Olson | ......................... | 600/15 |
| 6,265,984 B1 | 7/2001 | Molinaroli | | |
| 6,461,377 B1 * | 10/2002 | An | .............................. | 607/96 |
| 6,626,818 B2 | 9/2003 | Sexton | | |
| 6,648,812 B2 * | 11/2003 | Ardizzone | ..................... | 600/9 |
| 6,663,557 B2 * | 12/2003 | Werny | ......................... | 600/15 |
| 6,679,825 B2 | 1/2004 | Alicea | | |
| 6,781,697 B1 * | 8/2004 | Carra et al. | ................. | 356/446 |
| 2004/0122281 A1 | 6/2004 | Fischell et al. | | |
| 2004/0150372 A1 * | 8/2004 | Lee et al. | .................... | 320/148 |

OTHER PUBLICATIONS

Non-Final Office Action for U.S. Appl. No. 11/875,465, mailed Aug. 5, 2009, 14 pgs.

\* cited by examiner

*Primary Examiner*—Samuel G Gilbert
(74) *Attorney, Agent, or Firm*—Shane A. Kennedy

(57) ABSTRACT

A magnetic therapy device has been disclosed. In one embodiment of the magnetic therapy device, the device is disk-shaped, four inches in diameter, and ¾ inches thick. A disk with ten neodymium magnets mounted on the disk is mounted on a motor. The motor spins the disk, creating a dynamic magnetic field that may be useful for healing human tissue. The motor is powered by a rechargeable battery, which in turn is recharged via an inductive coil. The inductive recharging system allows the device to be completely sealed with no electrical contacts, making it safe to use near water. This embodiment also has a sequential controller which causes the device to become active for thirty minutes and then become inactive, and uses a tri-state LED to indicate the status of the device.

17 Claims, 11 Drawing Sheets

LI-ION BATTERY CHARGER

MAGNETIC THERAPY DEVICE

BACKGROUND OF THE INVENTION

Magnetic field therapy uses magnets to maintain health and treat illness. The human body and the earth naturally produce electric and magnetic fields. Electromagnetic fields can also be technologically produced, as with radio and television currents. Interactions between the body, the earth, and other electromagnetic fields are believed to cause physical and emotional changes in humans. Magnetic therapy is used for a wide range of health problems, including joint problems (such as arthritis), migraine headaches, pain (including mild to moderate pain after surgery and long-term pain), depression, cancer, and overstretched muscles or injuries to muscles, ligaments, and tendons. It is believed that magnetic therapy induces electrical fields within the bio-molecular structure and stimulates cells to correct abnormalities. However, many devices used in magnetic therapy are large and unwieldy, do not create an even or uniform magnetic field in the subject, are too complex for a lay person to use, or are subject to damage when exposed to water.

SUMMARY OF THE INVENTION

The present invention is a magnetic therapy device which utilizes at least one magnet mounted on a spinning disk to create a dynamic magnetic field. The disk is mounted on a motor which is powered by a battery, allowing the device to be portable. In one embodiment, the device has a housing that is disk-shaped, approximately the size of a hockey puck, and the housing is completely sealed with no electrical contacts on the outside of the housing, allowing it to be safely used in, for example, a bath tub.

BRIEF DESCRIPTION OF THE DRAWINGS

The accompanying drawings illustrate several aspects of embodiments of the present invention. The drawings are for the purpose only of illustrating preferred modes of the invention, and are not to be construed as limiting the invention. Part numbers and values for many of the components are shown in the circuit diagrams, and will be understood by one of ordinary skill in the art.

DESCRIPTION OF THE PREFERRED EMBODIMENTS

Figure 1:
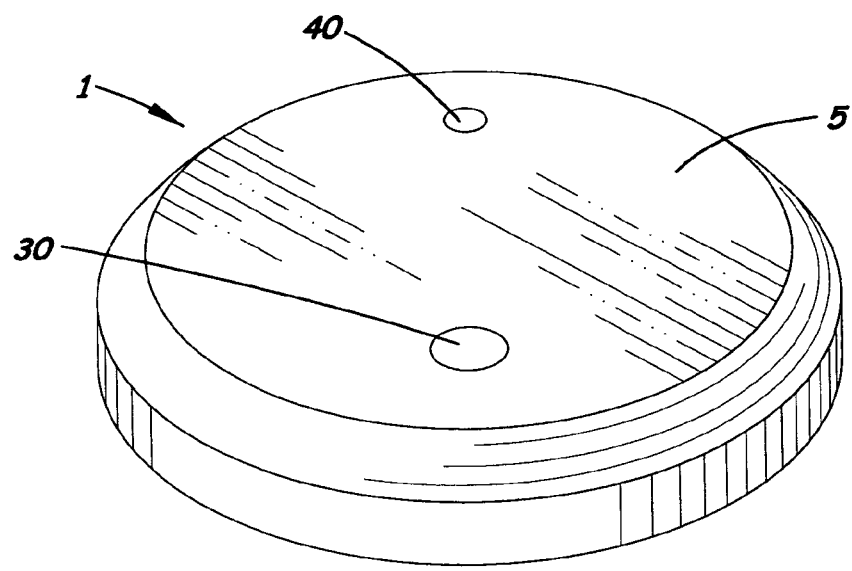
FIG. 1 shows a perspective view of the preferred embodiment of the magnetic therapy device, with the housing, probe insertion hole, and tri-state LED visible.
Figure 2:
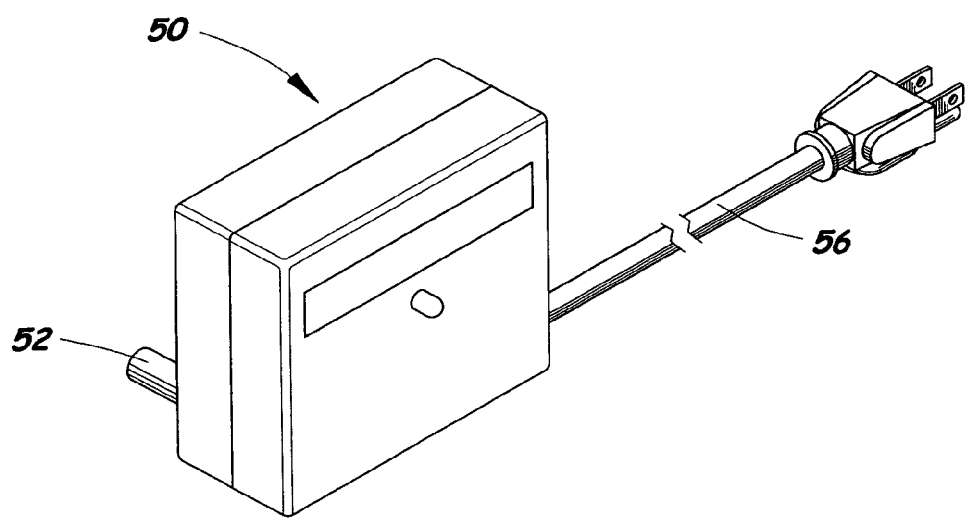
FIG. 2 shows a perspective view of the preferred embodiment of the inductive charging probe.

One embodiment of the magnetic therapy device 1 is comprised of four elements: (1) a magnetic field generator, which is comprised of a disk 10 with magnets 12 mounted thereon which, when rotating, generates a dynamic magnetic field; (2) a magnetic frequency generator, which comprises a DC motor 20 controlled by a magnetic field generator circuit 22 which controls the rotational speed of the DC motor; (3) the sequential logic controller circuit 44, which controls the therapy cycle and the tri-state LED 42 which indicates the status of the therapy cycle and the rechargeable battery 36; and (4) a rechargeable battery 36 which is part of the battery charging circuit 34 which enables the battery 36 to be recharged without any electrical contacts. An inductive probe 50 is used to recharge the battery 36 without any electrical contacts. In this embodiment, the four elements of the magnetic therapy device 1 are made entirely of non-magnetic material, except for the magnets 12 and motor 20, because any magnetic material within close proximity of the magnets 12 would create a magnetic drag, requiring more power to the motor 20 to maintain the rotational speed of the disk 10, reducing the efficiency of the device.

In one embodiment, the four elements of the single magnetic therapy device 1, which comprises a single rotating disk 10, are contained in a single housing 5 which is completely sealed and water proof, enabling the device to be used in a bathtub during therapy and handwashed, if desired; only the probe insertion hole 30 and the tri-state LED 40 are visible from the outside. The device is four inches in diameter and 34 inches thick and disk-shaped in this embodiment, approximately the size and shape of a hockey puck. This embodiment of the device is round and dark gray, and resembles a smooth river stone. This small size allows it to be easily held in one hand and used to massage or otherwise contact a user's body during magnetic therapy. It is believed that the device could be up to eight inches in diameter and two inches thick and still have this advantage. The self-controlled therapy cycle described below also makes the device easy to use. The small size, portability, and hand-held nature of the magnetic therapy device enable the magnetic therapy device to be used without any parts outside the disk-shaped housing 5, such as a stand, seat, or handles, once the battery 36 has been sufficiently charged.

Figure 3A:
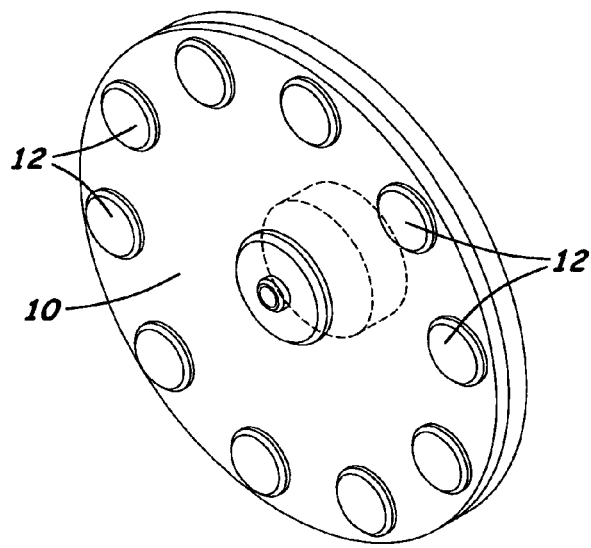
FIG. 3a shows a side perspective view of the preferred embodiment of the disk with ten rare earth magnets mounted on the top surface of the disk in a circular pattern with equal spacing.
Figure 3B:
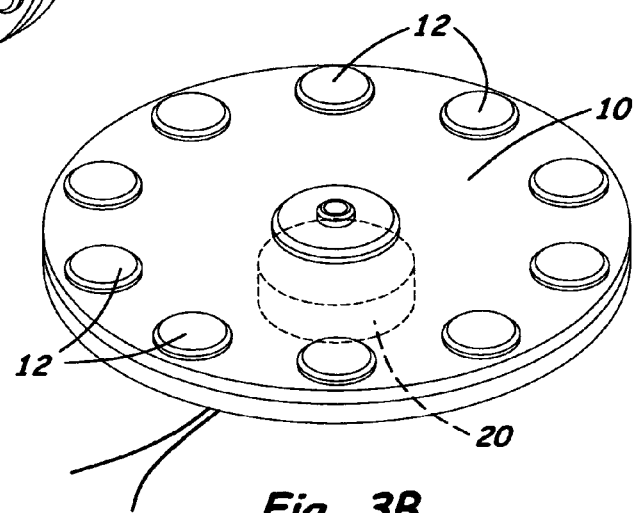
FIG. 3b shows a top perspective view of the preferred embodiment of the disk with ten rare earth magnets mounted on the top surface of the disk in a circular pattern with equal spacing, and also shows the motor attached to the disk.
Figure 4:
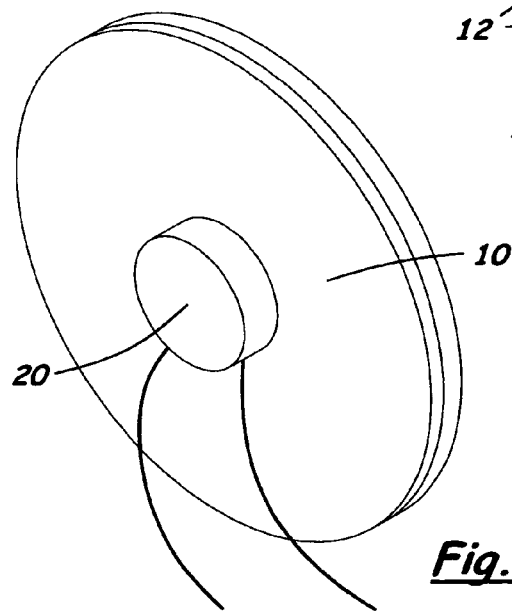
FIG. 4 shows a bottom perspective view of the preferred embodiment of the disk and shows the motor attached to the disk.

The magnetic field generator, shown in FIGS. 3a, 3b, and 4, begins with the disk 10. In one embodiment, the disk 10 is three inches in diameter and less than half an inch thick. The disk is made of a non-magnetic material, such as plastic or fiberglass FR-4. Magnets 12 are mounted on the top surface of the disk 10 by means of a press fit or by epoxy in a circular pattern with even spacing and alternating polarities. The alternating polarities of the magnets 12 creates a dynamic, sinusoidal magnetic field when the disk 10 spins. The device will function to create a dynamic or changing magnetic field as long as at least one magnet 12 is mounted on the disk 10; however, the more magnets 12 are mounted on the disk 10, the higher the frequency of the magnetic field. In one embodiment, ten rare earth magnets 12, namely neodymium magnets, are mounted on the disk 10. Neodymium magnets are a member of the Rare Earth magnet family and are the most powerful permanent magnets in the world. They are also referred to as NdFeB magnets, or NIB, because they are composed mainly of Neodymium (Nd), Iron (Fe) and Boron (B). The neodymium magnets 12 used in this embodiment are circular, ⅜ inches in diameter, and 3/16 inches thick. These neodymium magnets 12 generate a magnetic field strength of 100,000 Gauss when the disk 10 is spinning in this embodiment.

The use of a disk 10 ("disk" being defined as an object that is generally circular, has generally even thickness, and has a diameter greater than its thickness), which is contained inside the accompanying housing 12, which is also disk-shaped as previously defined in this sentence, enables the device to have all of the magnets 12 near the user's body, allowing for good depth penetration of the magnetic field into the user's body. The use of a disk 10 with the magnets 12 mounted on the top surface of the disk 10 also allows all magnetic poles to be equidistant from the user's body, which creates a more therapeutic magnetic field. The equal spacing of the magnets 12 in a circular pattern with alternating polarities allows the magnetic field to vary in a sinusoidal manner.

The disk 10 is secured to the shaft of a DC motor 20; in one embodiment, the means of securement is epoxy. Because the shaft is considered part of the DC motor 20, the disk 10 may be considered to be "mounted" on the DC motor 20. The DC motor 20 causes the disk 10 to rotate on an axis passing through the center of the disk which is perpendicular to the top and bottom surfaces of the disk 10, creating the dynamic magnetic field. By mounting the disk 10 onto a small DC motor 20, the magnetic therapy device can be manufactured with a disk-shaped housing 5 with no need for pulleys, resulting in a smaller and more efficient device. The DC motor 20 is connected (directly or indirectly) to the housing 5, and contained entirely within the housing 5. In one embodiment, the DC motor 20 is mounted to an electronic component circuit board, and the electronic component circuit board is secured to the housing 5. A DC motor 20 is used so that the device can be powered by a battery 36 and easily handled rather than needing to be attached to a cord which is plugged into a wall. In the embodiment described herein, the battery 36 is rechargeable; non-rechargeable batteries could also be used, but would require the housing 5 to be unsealed to replace the batteries when they run out.

The motor 20 has varying rotational speeds to allow the strength and frequency of the magnetic field to be varied. The relationship between the frequency of the magnetic field and the rotational speed of the disk 10 is $f=n \times rpm/120$, where f is the frequency of the magnetic field, n is the number of magnetic poles or magnets 12, and rpm is the number of revolutions per minute of the disk 10.

Figure 5:
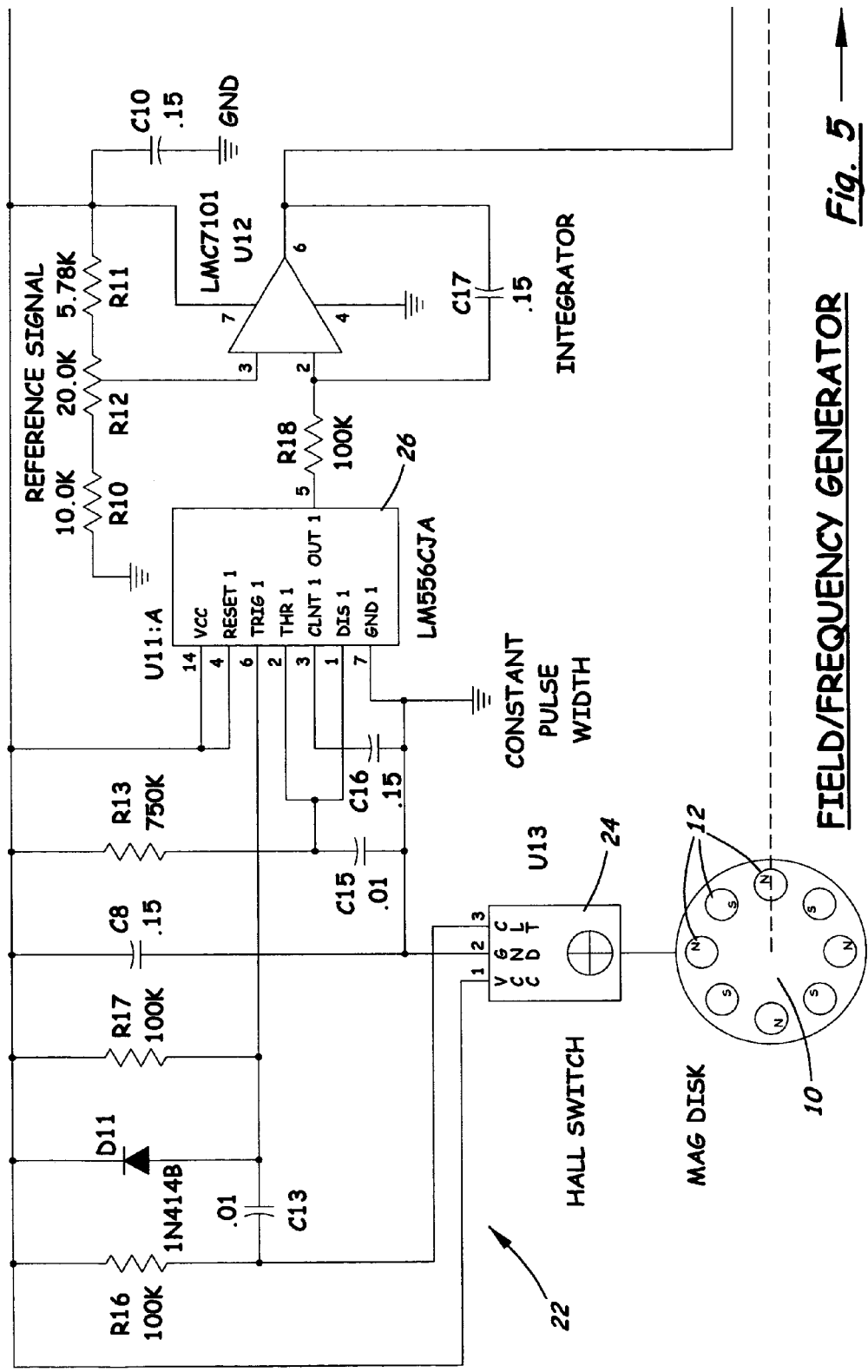
FIG. 5 is a circuit diagram showing an embodiment of the magnetic field generator circuit that determines the magnetic field frequency by controlling the rotational speed of the DC motor.
Figure 5:
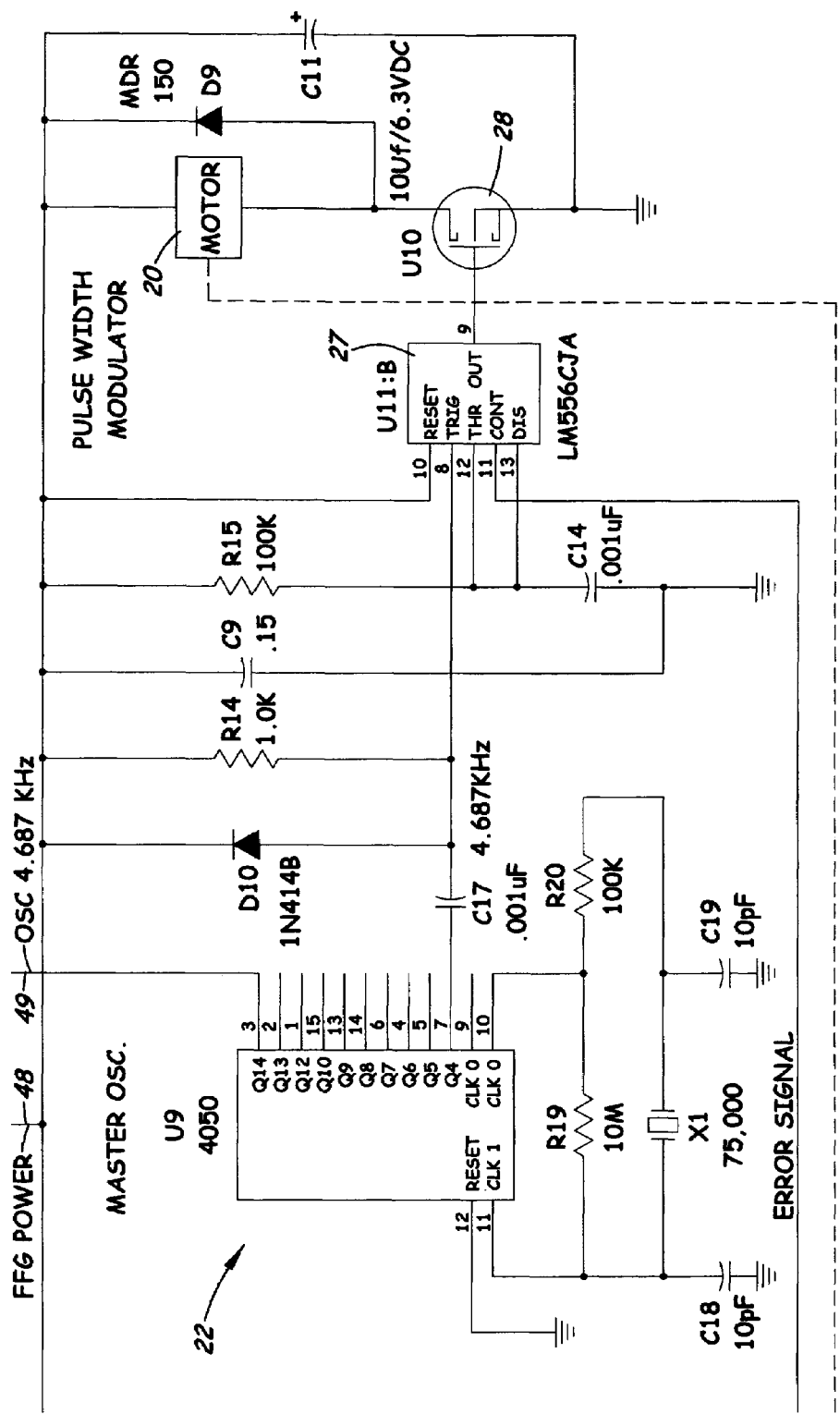

The magnetic frequency generator circuit 22 controlling the motor 20 could take on different designs depending on the type of motor 20, which could be a brush type, brushless type, or stepper type, among others. One embodiment uses a brush type motor 20 because it is relatively inexpensive and efficient in terms of power versus torque; the circuitry 22 used in this embodiment is shown in FIG. 5. The magnetic frequency generator circuit 22 of this embodiment receives two inputs from the sequential controller circuit 44: (1) field frequency generator power 48, and (2) oscillation frequency 49, which, in this embodiment, is 4.687 kHz.

A latching hall effect switch 24 creates a feedback path for the motor 20. The latching hall effect switch 24 also generates a pulse for each cycle of the sinusoidal magnetic wave. The pulse triggers a first monostable multivibrator 26; the output of the first monostable multivibrator 26 is a precise pulse width which remains constant regardless of the rotational speed of the disk 10. This precise output pulse of the first monostable multivibrator 26 is fed into an operational amplifier configured as an integrator. The output pulse of the first monostable multivibrator 26 is compared to a reference signal determined by a potentiometer. The integrator output is the error signal that exists between the reference signal, which represents the desired speed of the sinusoidal magnetic wave, and the precession pulse of the hall effect switch 24, which represents the actual speed of the sinusoidal magnetic wave.

This error signal is used to control the pulse width of a second monostable multivibrator 27. This second monostable multivibrator 27 is essentially a pulse width modulator that is triggered to generate an output pulse at a rate of 4.55 kHz; the pulse width of the output pulse is a function of the error signal. The second monostable multivibrator 27 or pulse width modulator drives the motor 20 through a MOSFET 28. The pulse width, which increases with the degree of error that exists between the actual speed and reference or desired speed of the sinusoidal magnetic wave, causes the motor 20 to turn the shaft faster, bringing the speed of the motor 20 to the desired speed.

Figure 6:
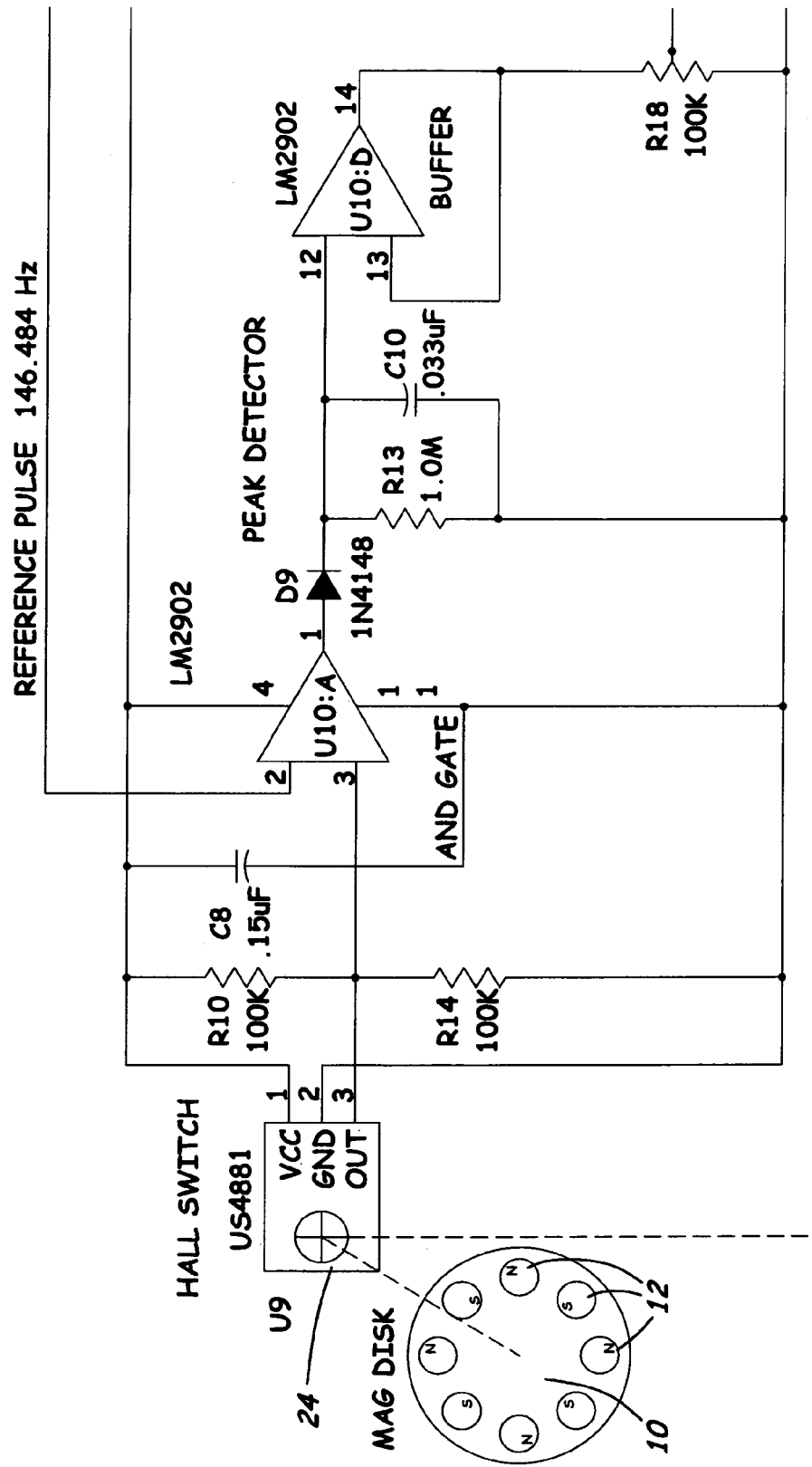
FIG. 6 is a circuit diagram showing an alternative embodiment of the magnetic field generator.
Figure 6:
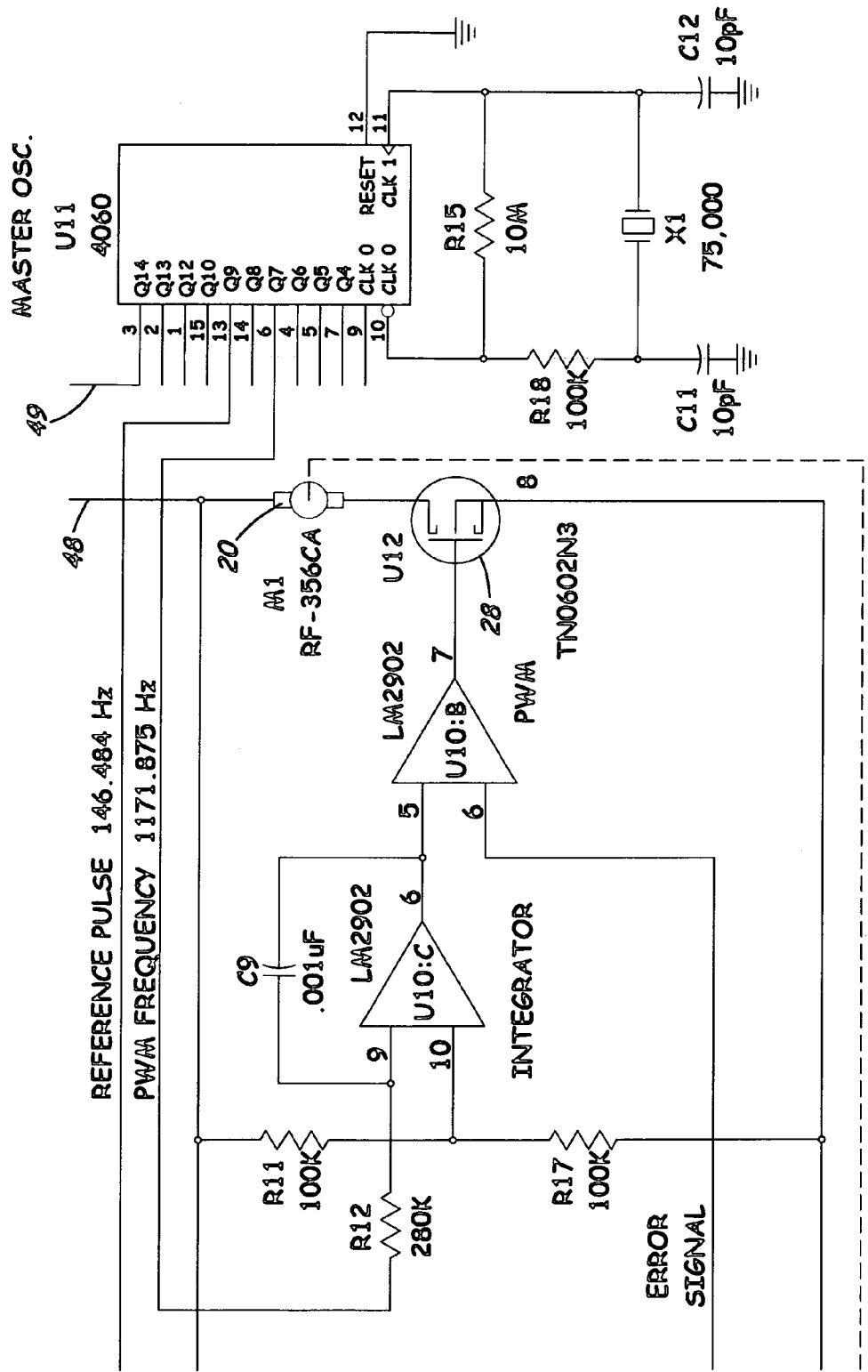

An alternative embodiment for the circuitry of the magnetic frequency generator is shown in FIG. 6.

In an embodiment using a stepper type motor 20, the controls needed to maintain a constant speed of rotation for the disk 10 would be considerably simpler. The controls would require a stepper motor driver integrated circuit; the speed would be controlled by the input frequency of the motor driver. There would be no need for a feedback path. However, stepper type motors are currently more expensive than brush type motors.

Figure 7:
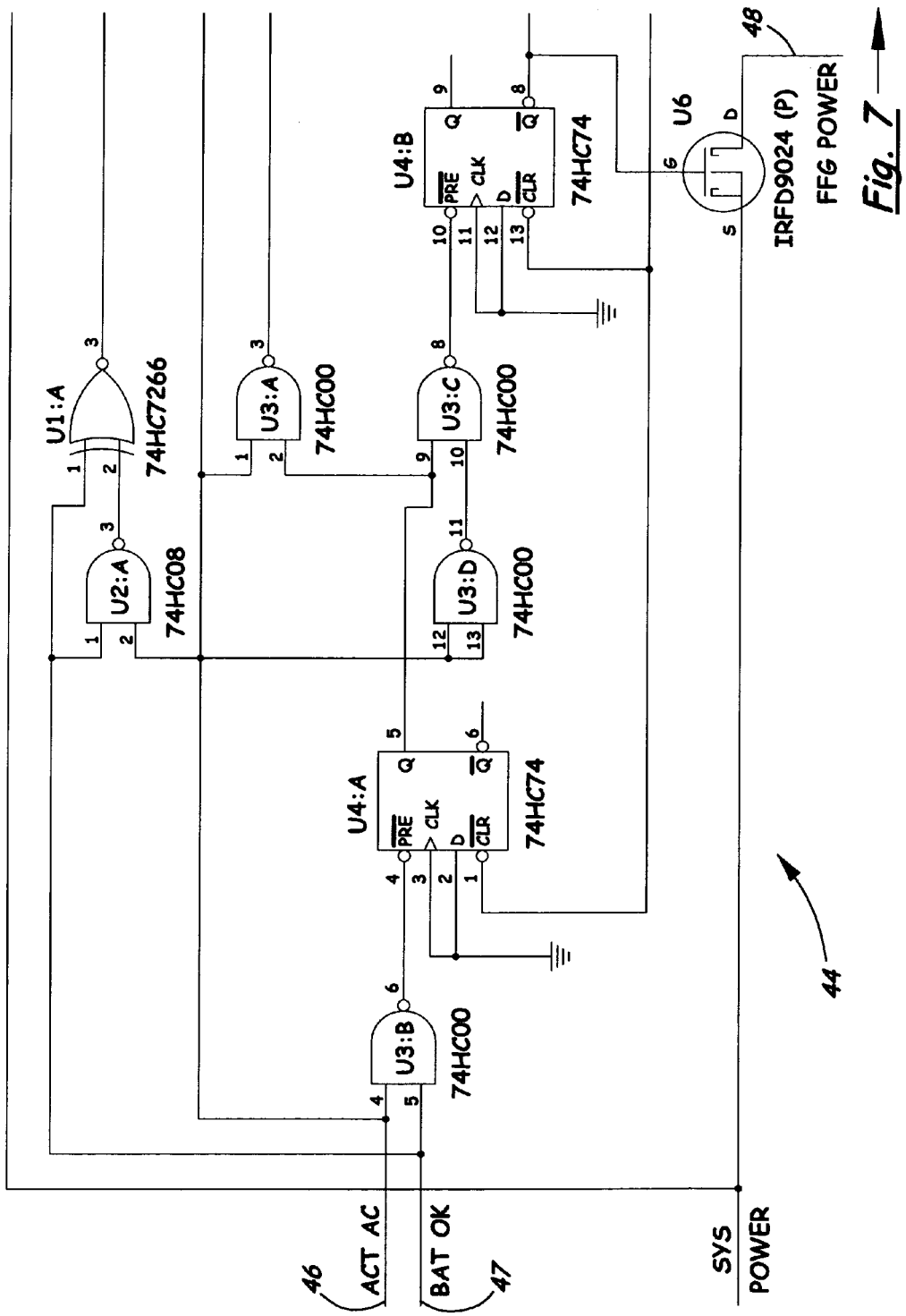
FIG. 7 is a circuit diagram showing the preferred embodiment of the circuit for the sequential controller, which determines when the therapy cycle begins and ends and controls the tri-state LED indicator.
Figure 7:
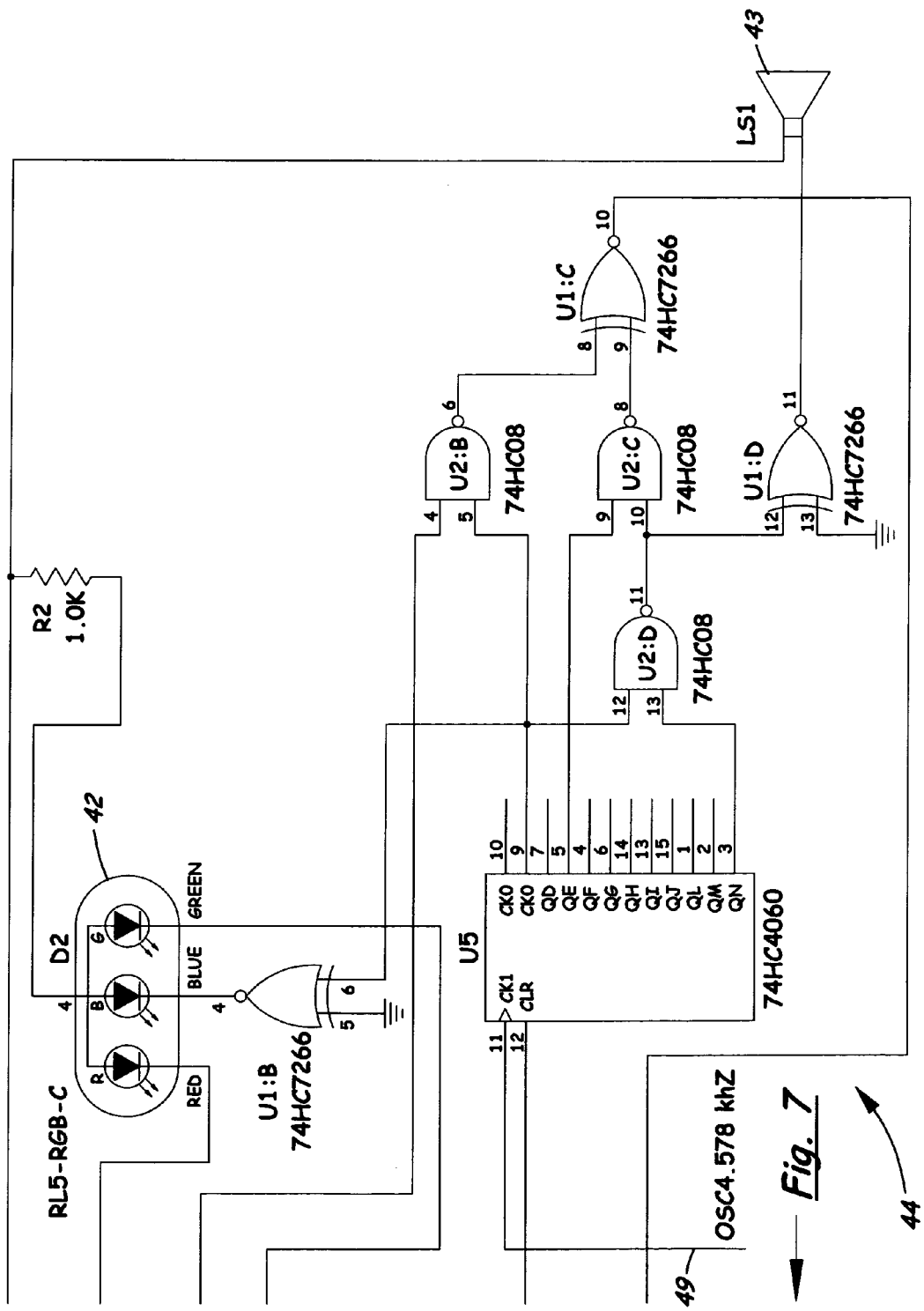
Figure 8:
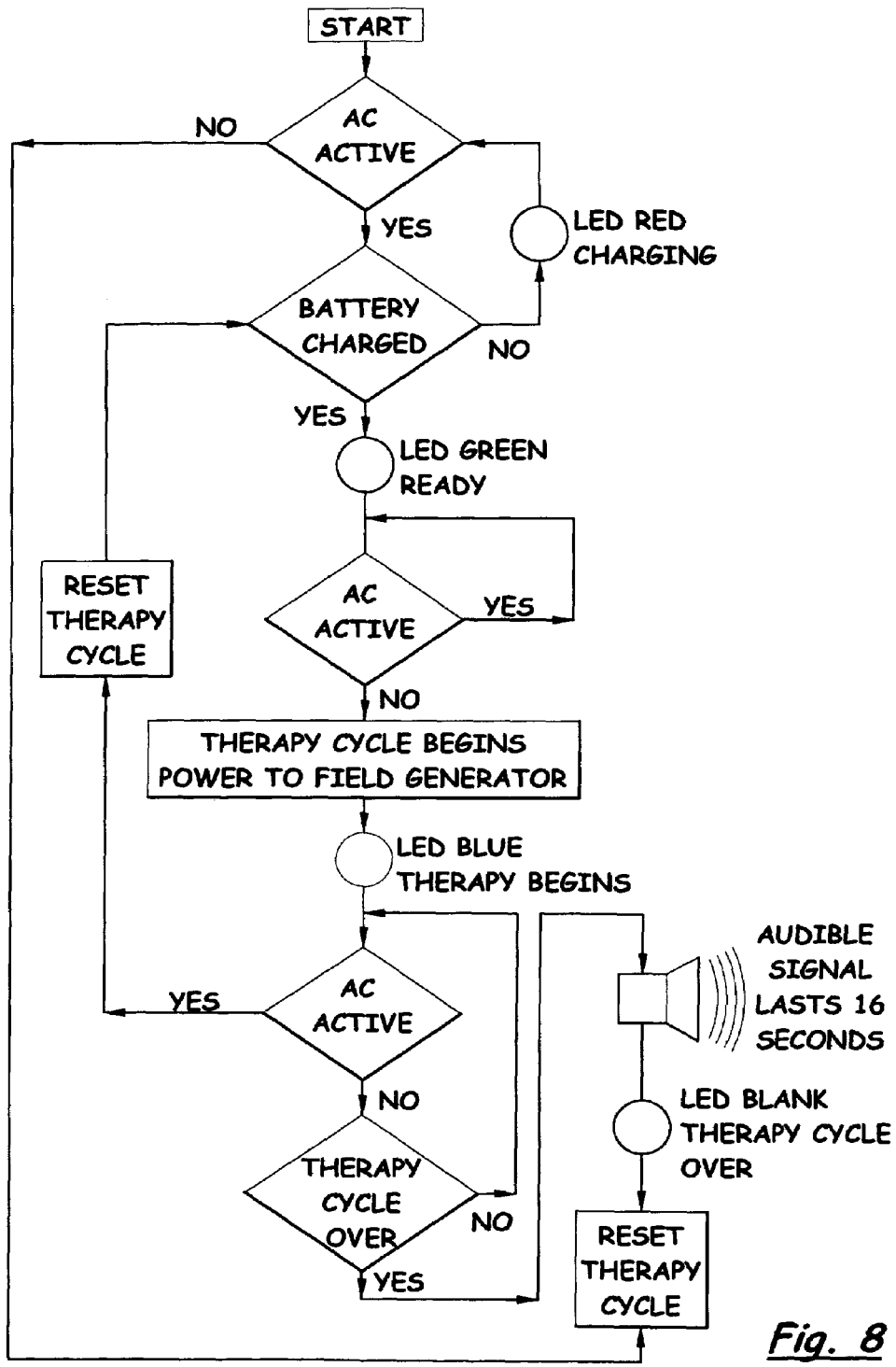
FIG. 8 is a flow chart showing the logical steps taken by the sequential controller in the preferred embodiment.

The sequential controller circuit 44, shown in FIG. 7, controls the therapy cycle. The sequential controller circuit 44 receives two signals from the battery charging circuit 34: (1) AC active 46, which is high when the ferrite rod 52 of the inductive probe 50 is in place and generating a high frequency magnetic field inside the probe insertion hole 30, and low when no such high frequency magnetic field is present inside the probe insertion hole 30; and (2) battery charged 47, which is high when the battery 36 is sufficiently charged to enable it to power one full therapy cycle, and low when the battery 36 is not sufficiently charged. The sequential controller circuit 44 uses high speed 74HC family CMOS integrated circuits to implement the design. The timing events take place with great accuracy due to the crystal time base X1. In the embodiment shown, the crystal time base X1 has a frequency of 75 kHz and a tolerance of ∓0.005%.

The sequential controller circuit 44 enables the inductive charging probe 50 to be used to start the therapy cycle. If the magnetic therapy device is inactive and the AC active signal 46 is low, meaning that there is no magnetic field present in the probe insertion hole 30 and receiver coil 32, then the magnetic therapy device will remain inactive. If the battery charged signal 47 is high, meaning that the battery has sufficient charge to power at least one therapy cycle, and the AC active signal 46 is high, meaning that there is a magnetic field present in the probe insertion hole 30 and receiver coil 32, then the sequential controller circuit 44 will wait for the AC active signal 46 to become low, at which point it will begin the therapy cycle by causing the motor 20 to spin the disk 10 for thirty minutes. With sixteen seconds left in the therapy cycle, a speaker 43 will emit an audible signal, informing the user that the therapy cycle is almost over. After thirty minutes, the sequential controller circuit 44 will cause the motor 20 to stop spinning the disk 10, ending the therapy cycle.

In one embodiment, the tri-state LED 42 has three colors, namely red, green, and blue, which indicate the status of the battery 20 and the therapy cycle. The tri-state LED 42 emits red when the motor 20 is not causing the disk 10 to spin, the AC active signal 46 is high, meaning that the battery 36 is charging, and the battery charged signal 47 is low, meaning that the battery 36 does not have sufficient charge to power a full therapy cycle. The tri-state LED 42 emits green when the motor 20 is not causing the disk 10 to spin, the AC active signal 46 is high, meaning that the battery 36 is charging, and the battery charged signal 47 is high, meaning that the battery 36 does have sufficient charge to power a full therapy cycle. The tri-state LED 42 emits blue when the therapy cycle is in effect and the motor 20 is causing the disk 10 to spin. When the therapy cycle is not in effect, meaning that the motor 20 is not causing the disk 10 to spin, and the AC active signal 46 is low, the tri-state LED 42 is blank, not emitting any color.

Figure 9:
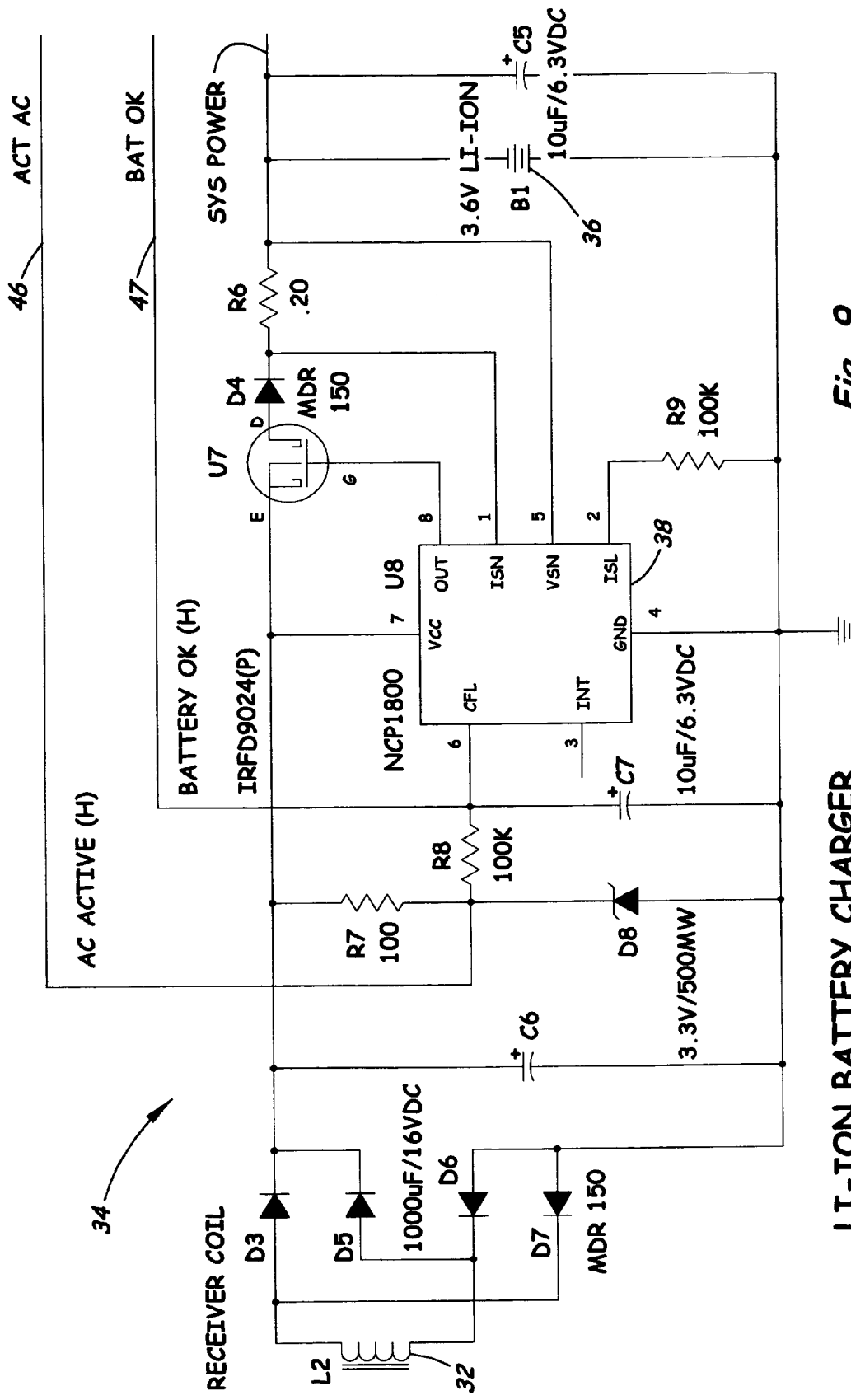
FIG. 9 is a circuit diagram showing the preferred embodiment of the battery charging circuit.

FIG. 9 is a flowchart showing the above-described pattern of events. When the therapy cycle is over or not in effect, the tri-state LED 42 is blank. When the inductive charging probe 50 is inserted into the probe insertion hole 30, causing the AC active signal 46 to become high, the sequential controller circuit 44 checks the battery charged signal 47. If the battery charged signal 47 is low, then the tri-state LED 42 will emit red until one of two events happens: (1) the AC active signal 46 becomes low, at which point the therapy cycle will be reset and the tri-state LED 42 will go blank; or (2) the battery charged signal 47 becomes high, at which point the tri-state LED 42 will emit green. With the battery charged signal 47 high and the AC active signal 46 high, the battery 36 is charging (unless it is fully charged), and the tri-state LED 42 emits green until the AC active signal 46 becomes low. When the AC active signal 46 becomes low, the therapy cycle begins, and the tri-state LED 42 emits a flashing blue signal while the therapy cycle is in effect. Sixteen seconds before the therapy cycle has run its thirty-minute course, the speaker 43 emits an audible signal, and at the end of the thirty minutes, the therapy cycle ends, the motor 20 stops causing the disk 10 to spin, and the tri-state LED becomes blank. The therapy cycle can be restarted by inserting and removing the inductive charging probe 50 from the probe insertion hole 30.

It is envisioned that different time durations than thirty minutes could be used for the therapy cycle. Also, design alternatives to the shown circuitry include a microcontroller operating under software control or a microprocessor, either of which could utilize an infrared data link to enable non-contact programming of the magnetic field frequency, duration of therapy, and individual program profiles. Or, a programmable logic array could be used. These design alternatives would be advantageous for large scale production. It is also envisioned that instead of using the inductive charging probe 50 to control the therapy cycle, a button could be installed onto the housing 5 and connected to the sequential controller circuit 44 to control the therapy cycle; the button should be designed to prevent any water or other liquid from entering the device from outside the housing.

In one embodiment of the power supply, the battery 36 is rechargeable and non-magnetic. The battery 36 is rechargeable so that the device can be reused without having to disassemble the device and replace the battery 36, allowing the device to be completely sealed and waterproof. The battery 36 is non-magnetic so that it will not create a magnetic drag on the disk 10. In one embodiment, the battery 36 is a 3.7 volt, 1500 milliampere-hour, Prismatic Lithium-Ion battery. This terminal voltage of 3.7 volts is high enough to operate the electronic components of the magnetic therapy device without using a step-up DC to DC converter. This Prismatic Lithium-Ion battery, which is a Prismatic Polymer type, is non-magnetic, and has the highest energy density of all available rechargeable batteries, allowing the device to be small and efficient. The Prismatic Lithium-Ion battery can be recharged many times, and can operate the magnetic therapy device for at least twenty continuous hours before recharging, allowing for forty back-to-back thirty-minute therapy cycles before the device needs to be recharged for two hours.

Figure 10:
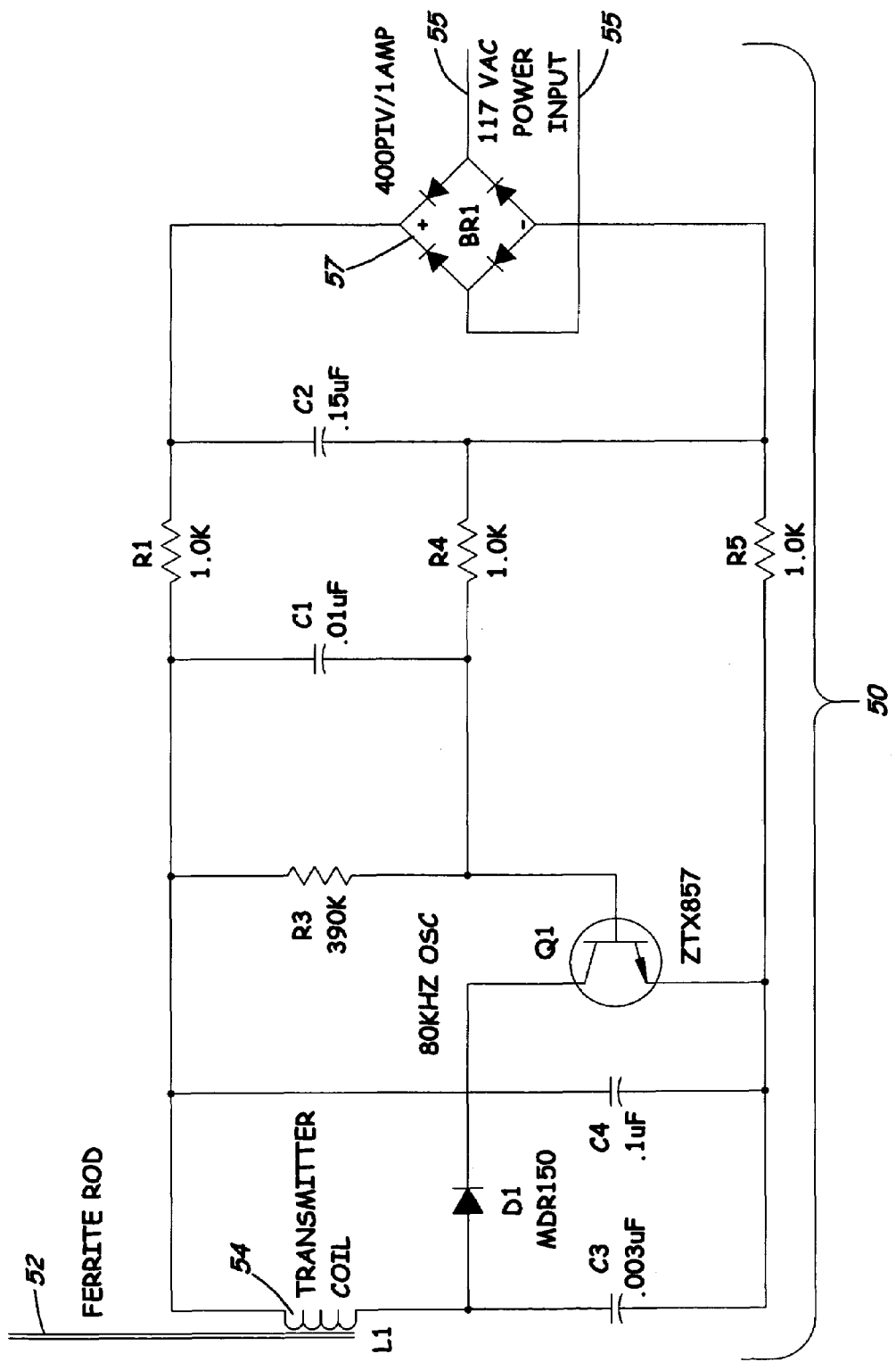
FIG. 10 is a circuit diagram showing the preferred embodiment of the circuitry for the inductive probe that generates the magnetic field used to charge the battery.

The battery charging circuit 34, shown in FIG. 10, receives power from an inductive coil, the receiver coil 32. The receiver coil 32 receives power from a high frequency magnetic field created by the transmitter coil 54 of the battery charging circuit 50. The receiver coil 32 is inductively coupled to the transmitter coil 54 by a ferrite rod 52 when the inductive charging probe 52 is inserted into the probe insertion hole 30. The receiver coil 32 surrounds the probe insertion hole 30; the probe insertion hole 30 is a recessed portion of the housing 30 and is made from the same material as the housing 5. The magnetic field created by the transmitter coil 54 and ferrite rod 52 induces a high-frequency AC current in the receiver coil 32. This high-frequency current output from the receiver coil 32 is rectified using high speed diodes in a bridge configuration (D3, D5, D6, D7). This rectified current is converted to DC using an electrolytic filtering capacitor (C6).

Recharging Lithium-Ion batteries requires a special charging sequence of current and voltage. In one embodiment, this charging sequence is handled in the battery charging circuit 34 by a Motorola NCP1800 integrated circuit 38. The battery charging circuit 34 shares two control signals with the sequential controller circuit 44: AC active 46, and battery charged 47. These control signals 46, 47, in combination with the battery charging circuit 50, enable the battery 36 to be fully recharged by the magnetic field generated by the transmitter coil 54 and ferrite rod 52. The combined circuitry of the sequential controller circuit 44 and the battery charging circuit 34 causes the therapy cycle to begin when the inductive charging probe 52 is removed from the probe insertion hole 30 if the battery 36 was sufficiently charged to power one full therapy cycle.

The circuitry for one embodiment of the inductive charging probe 50 is shown in FIG. 10. The inductive charging probe 50 generates a well focused magnetic field to power the receiver coil 32 and the battery 36. The inductive charging probe 50 also serves as operator control of the magnetic therapy device by controlling the voltage of the receiver coil 32. The use of the inductive charging probe 50 as operator control obviates the need for switches or moving parts outside the housing 5. When the inductive charging probe 50 is removed from the probe insertion hole 30, the receiver coil 32 voltage drops to zero, and if the battery 36 was sufficiently charged to power one full therapy cycle, then the therapy cycle will begin. This enables the battery 36 to be charged and the magnetic therapy device to be controlled in a completely sealed housing 5 without any electrical contacts outside the housing 5. Thus, the magnetic therapy device will still operate even if it completely submerged in water and used in a bathtub without risk of electric shock.

The ferrite rod 52 is part of the inductive charging probe 50 and is inductively coupled to the transmit coil 54. The transmit coil 54 is operated at high frequency, typically 85 kHz. This frequency is needed to increase the efficiency of the coupling between the transmitter coil 54 and the receiver coil 32 because the magnetic geometry between these two elements is not ideal, resulting in a loss of power.

The power input 55 of the inductive charging probe 50 receives 117 Volts AC from a wall outlet. This AC input is rectified with a bridge rectifier 57, and this rectified wave is converted to high voltage DC by a second electrolytic capacitor C2. A high voltage NPN transistor Q1 configured as an RC oscillator is operated by DC voltage from a first electrolytic capacitor C2 and drives the transmitter coil 54 at 85 kHz.

Although this invention has been described above with reference to particular means, materials and embodiments, it is to be understood that the invention is not limited to these disclosed particulars, but extends instead to all equivalents within the scope of the following claims.

I claim:

1. A magnetic therapy device comprising:
   a disk with a plurality of magnets mounted on the disk;
   wherein the disk is mounted on a motor and the motor is configured to cause the disk to spin when the motor is active;
   wherein the motor is powered by a battery;
   wherein the motor is mounted on a housing;
   wherein the motor is connected to a circuit inside the housing which is configured to cause the motor to become active for a finite duration of time and then become inactive before the battery has been drained of power;
   wherein the magnetic therapy device further comprises a receiver coil which is configured to receive power from a magnetic field and transfer the power to the battery; and
   wherein the circuit is configured to cause the motor to become active when an inductive probe is taken away from the receiver coil.

2. The magnetic therapy device of claim 1, wherein the magnetic therapy device is configured to maintain a constant motor speed by comparing a magnetic frequency of the disk to a reference signal.

3. The magnetic therapy device of claim 1 wherein the housing has a diameter no greater than eight inches.

4. The magnetic therapy device of claim 1 wherein the housing has a diameter no greater than eight inches and a thickness no greater than two inches.

5. The magnetic therapy device of claim 1 wherein the magnetic therapy device is configured to operate while submerged in water.

6. The magnetic therapy device of claim 1 wherein a center of the disk is secured to a shaft of the motor.

7. The magnetic therapy device of claim 6 wherein the plurality of magnets comprises at least ten magnets mounted on top of the disk in a circular pattern with equal spacing and alternating polarities.

8. The magnetic therapy device of claim 1 wherein the housing is waterproof.

9. The magnetic therapy device of claim 8 wherein the housing is made of non-magnetic material.

10. The magnetic therapy device of claim 9 wherein the magnetic therapy device comprises no electrical contacts outside the housing.

11. A magnetic therapy device comprising:
    a housing;
    a motor mounted on the housing and configured to:
       cause a disk to spin when the motor is active; and
       receive power from a battery;
    the disk mounted on the motor, the disk having a plurality of magnets mounted on the disk;
    a battery configured to provide power to the motor;
    a receiver coil configured to receive power from a magnetic field and transfer the power to the battery;
    a circuit inside the housing configured to:
       cause the motor to become active for a finite duration of time and then become inactive before the battery has been drained of power; and
       cause the motor to become active when an inductive probe is taken away from the receiver coil.

12. The magnetic therapy device of claim 11, wherein an outside surface of the housing comprises no electrical contacts.

13. The magnetic therapy device of claim 11 wherein the housing encloses the motor, the disk, the receiver coil, and the circuit, and the housing is waterproof.

14. The magnetic therapy device of claim 11 wherein the magnetic therapy device is configured to operate while submerged in water.

15. The magnetic therapy device of claim 11 wherein the plurality of magnets comprises at least ten magnets mounted on top of the disk in a circular pattern with equal spacing and alternating polarities.

16. The magnetic therapy device of claim 11, wherein the circuit includes an integrated circuit configured to maintain a constant speed of rotation of the disk.

17. The magnetic therapy device of claim 11, wherein the magnetic therapy device is configured to maintain a constant motor speed by comparing a magnetic frequency of the disk to a reference signal.

* * * * *

UNITED STATES PATENT AND TRADEMARK OFFICE
CERTIFICATE OF CORRECTION

| | | |
|---|---|---|
| PATENT NO. | : 7,648,454 B2 | Page 1 of 1 |
| APPLICATION NO. | : 11/247365 | |
| DATED | : January 19, 2010 | |
| INVENTOR(S) | : George Sotiriou | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 642 days.

Signed and Sealed this

Twenty-eighth Day of December, 2010

David J. Kappos
*Director of the United States Patent and Trademark Office*